(12) United States Patent
Engelhardt

(10) Patent No.: US 8,604,698 B2
(45) Date of Patent: Dec. 10, 2013

(54) ILLUMINATION FOR A TEST DEVICE

(75) Inventor: Franz Engelhardt, Starnberg (DE)

(73) Assignee: Giesecke & Devrient GmbH, Munich (DE)

( * ) Notice: Subject to any disclaimer, the term of this patent is extended or adjusted under 35 U.S.C. 154(b) by 541 days.

(21) Appl. No.: 12/935,501

(22) PCT Filed: Mar. 30, 2009

(86) PCT No.: PCT/EP2009/002306
§ 371 (c)(1),
(2), (4) Date: Sep. 29, 2010

(87) PCT Pub. No.: WO2009/121545
PCT Pub. Date: Oct. 8, 2009

(65) Prior Publication Data
US 2011/0018469 A1  Jan. 27, 2011

(30) Foreign Application Priority Data
Mar. 31, 2008 (DE) .......... 10 2008 016 461

(51) Int. Cl.
*H05B 37/00* (2006.01)
(52) U.S. Cl.
USPC ............ 315/119; 315/127; 315/306; 315/312
(58) Field of Classification Search
USPC ........... 315/85, 88, 89, 90, 93, 119, 121, 125, 315/127, 128, 185 R, 192, 193, 210, 297, 315/298, 306, 307, 310, 312, 313, 320, 316, 315/362
See application file for complete search history.

(56) References Cited

U.S. PATENT DOCUMENTS

| | | | |
|---|---|---|---|
| 7,293,885 B2 | 11/2007 | Kramer et al. | |
| 7,714,302 B2 | 5/2010 | Braumandl | |
| 2003/0103198 A1* | 6/2003 | Yu | 356/71 |
| 2004/0165393 A1 | 8/2004 | Abe et al. | |

FOREIGN PATENT DOCUMENTS

| | | |
|---|---|---|
| CN | 2379350 Y | 5/2000 |
| DE | 20209221 U1 | 10/2002 |
| DE | 202004021104 U1 | 11/2006 |
| DE | 102006032701 B3 | 1/2008 |
| EP | 0762174 A2 | 3/1997 |
| GB | 2353726 A | 3/2001 |

OTHER PUBLICATIONS

Search report of German Patent Office regarding German Patent Application 10 2008 016 461.5, Jan. 22, 2009.
International Search Report in PCT/EP2009/002306, Jul. 24, 2009.

* cited by examiner

*Primary Examiner* — Douglas W Owens
*Assistant Examiner* — Jianzi Chen
(74) *Attorney, Agent, or Firm* — Workman Nydegger

(57) ABSTRACT

A lighting arrangement comprises a checking device and a method for the control thereof, with a sensor device containing at least one light source, where the at least one light source radiates light with high radiant power which represents a danger to the eyes of operators or service personnel. A housing, which contains the at least one light source and prevents an emergence of light of the light source, is monitored as to whether the housing is open, where the at least one light source with high radiant power is switched off if there is detected upon the monitoring an opening of the housing, which permits an emergence of light of the light source. It is provided here that a lighting arrangement is switched on at the same time or later which has a radiant power not representing any danger to the eyes of operators or service personnel.

13 Claims, 1 Drawing Sheet

ILLUMINATION FOR A TEST DEVICE

FIELD OF THE INVENETION

The present invention relates to a lighting means for a checking device and a method for the control of such a lighting means.

BACKGROUND

The mentioned checking devices are, for example, automatic sorting, checking and/or counting apparatuses for sheet material such as in particular bank notes, checks, identification documents, share certificates/documents of value or other documents. Moreover, checking devices are concerned which can be generally used to check objects as to the presence or absence of certain properties. The further description relates by way of example to the first mentioned checking devices for sheet material.

So as to check the sheet material within such devices for example as to type, authenticity, validity or damage, there are usually used, among other things, optical sensor devices. In the sensor devices the sheet material is illuminated with special light sources, and the light reflected by the sheet material or transmitted through the sheet material is measured and evaluated by corresponding sensors. For spectroscopic examinations light with certain wavelengths and a radiant power as high as possible is required here.

A device for the lighting of sheet material is described in EP 0 762 174 A2. The lighting means here substantially consists of a plurality of mirror segments of cylindrical mirrors with elliptical base surface, which each have two focus lines. The mirror segments are arranged such that both the first and the second focus lines of all mirror segments are coincident in a first or second focus line, respectively. In the first common focus line there is arranged a light source consisting of a series of light emitting diodes. The light emitted by the light emitting diodes is focused by reflection at the mirror segments onto the sheet material located in the second common focus line, and so a line-shaped lighting for the sheet material with a relatively high illuminance is produced. This, however, is a relatively elaborate and sensitive set-up. Due to the use of light emitting diodes as a light source, the radiant power is limited.

To increase the detection sensitivity in the sensor device, however, higher radiant power is necessary. This is possible, for example, when more intense light sources, in particular laser light sources, in the visible (400 to 700 nm) and infrared (700 to 1400 nm) or ultraviolet (300 to 400 nm) range are used. Here, the use of laser diodes of the laser classes 3b and 4, of Nd:YAG lasers or other solid state lasers with continuous or pulsed radiation is particularly suitable. With the use of lasers, however, due to the high radiant power and the good focusability of the radiated light, there arises a relatively great risk for the eyes of operators or of service personnel of the apparatuses. Therefore, for conventional laser lighting there are applicable restrictive power limitations so as to ensure eye protection, which either allow an only very low laser power—which is very unhelpful for the intended use—or require extensive safety measurements.

A possibility to ensure the protection of employees is to provide the doors of a closed system with interrupt switches which lead to a switch-off of the laser when the doors are opened. In particular with the sheet material processing devices, however, it is often necessary to carry out service work with the doors open. This is the case for example when the transport path of the sheet material is set or places within the transport path have to be searched for where sheet material is damaged, or the sensor devices or parts thereof have to be cleaned because they were soiled by the processing of the sheet material. But this service work may possibly turn out to be very difficult, because due to the automatic switch-off of the laser light sources in the sensor device, the conditions present during normal operation are changed. For example, in such a case it is very difficult for the service personnel to recognize that, for example, the sensor device or parts thereof are soiled and have to be cleaned.

SUMMARY

The invention is based on the object of providing a lighting means for a checking device and a method for the control thereof, which ensure eye protection for operators or service personnel despite a use of intense lighting means, in particular laser light sources, but which also in the case of service work present conditions which largely correspond to the conditions during normal operation.

The invention here starts out from a lighting means for a checking device and a method for the control thereof, with a sensor device containing at least one light source, wherein the at least one light source radiates light with high radiant power which represents a danger to the eyes of operators or service personnel, wherein a housing, which contains the at least one light source and prevents an emergence of light of the light source, is monitored as to whether the housing is open, wherein the at least one light source with high radiant power is switched off if there is detected upon the monitoring an opening of the housing, which permits an emergence of light of the light source. It is provided here that a lighting means is switched on at the same time or later which has a radiant power not representing any danger to the eyes of operators or service personnel.

The invention has the particular advantage that at any time a protection of the eyes of operators or service personnel is ensured. Through the lighting also in the case of service work it is ensured that the conditions present during the service work largely correspond to the conditions present during normal operation. This makes it easier for operators or service personnel to carry out the necessary work.

In the following the invention is explained in more detail with reference to the accompanying Figures on the basis of an embodiment. The use of the term "laser" in the following is to be understood such that it covers all light sources which because of their radiant power fall under the laser safety regulations or have a luminous power which is so high that the eyes of operators or service personnel of the checking device are endangered thereby.

DETAILED DESCRIPTION OF VARIOUS EMBODIMENTS

Figure 1:
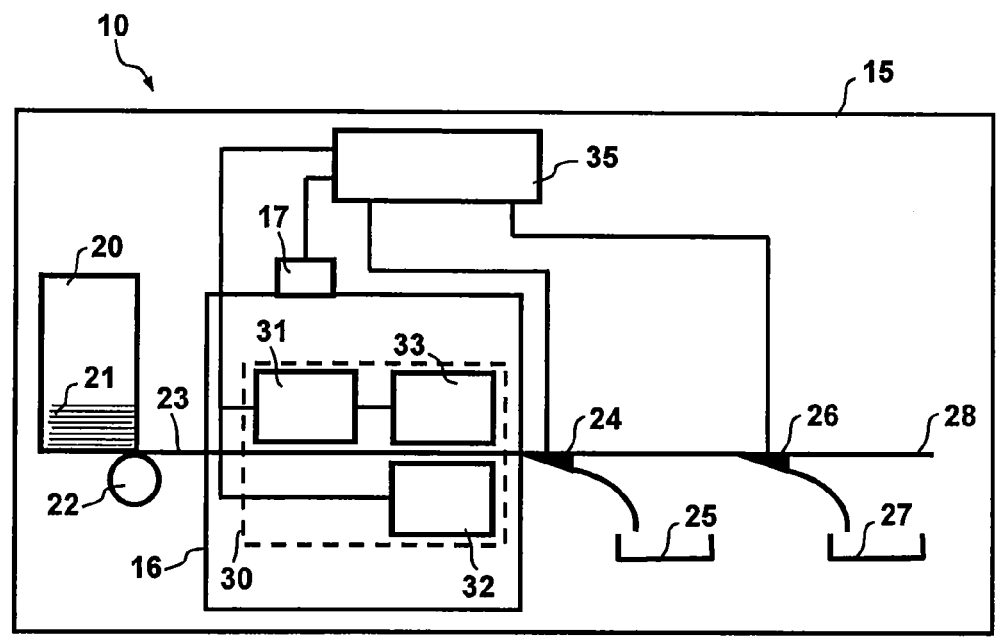
FIG. 1 shows a schematic representation of a checking device for sheet material with at least one lighting means.

FIG. 1 shows a schematic representation of a basic structure of a device 10 for the check of bank notes, in particular for the authenticity check of bank notes.

The device 10 for the check of bank notes is formed as a bank note processing machine and has an input pocket 20 for the feed of bank notes 21 to be processed, into which a singler 22 reaches. The singler 22 seizes one of the bank notes 21 to be processed at a time and transfers the single bank note to a transport system 23 which transports the single bank note through a sensor device 30.

In the sensor device 30 there are present, for example, different sensors 31, 32, 33 which can check different properties of the bank notes. For example, there may be present a first sensor 31 which detects light remitted by a first side of the bank note, a second sensor 32 which detects light remitted by a second side of the bank note, and a third sensor 33 which detects light transmitted through the bank note. For the check of bank notes the sensors 31, 32, 33 perform measurements upon which they capture properties of each single bank note and generate corresponding data. For this purpose, the sensors 31, 32, 33 may scan the bank notes with a specific resolution e.g. line by line in the form of image dots. Each of the sensors 31, 32, 33 here may contain at least one light source which produces light of a particular wavelength or of a particular wavelength range for the check of bank notes. The light sources may particularly be laser light sources. In the checking device described on the basis of FIG. 1, for example, at least one light source is contained in the first sensor 31 for the lighting of the first side of the respective bank note to be checked facing the first sensor 31. Likewise, for example at least one light source is contained in the second sensor 32 for the lighting of the second side of the respective bank note to be checked facing the second sensor 32. In the third sensor 33 one can do without a light source, since the third sensor 33 detects light transmitted through the respective bank note to be checked. In the present example this light comes from the light source of the second sensor 32 located opposite the third sensor 33.

From the scanned image dots of each of the bank notes the sensors 31, 32, 33 and/or a control unit 35 can generate data which represent any place on the surface of the respective bank note. The generation of the data can be effected e.g. for one side of the bank notes, i.e. for one of the surfaces of the bank notes, likewise, both surfaces can be scanned and corresponding data be made available. Preferably, the sides or surfaces of the bank notes each are completely scanned and corresponding data for the complete side or surface are generated.

From the data of the sensors 31, 32, 33 the control unit 35 derives properties which are relevant for the check of the bank notes. These properties characterize the state of the bank notes, such as e.g. soiling, spots, limpness, tears, adhesive tape, dog-ears, holes, missing components of the bank notes, etc., the type of the bank notes, such as e.g. currency, denomination, series, etc., and in particular the authenticity of the bank notes. The respective properties can be derived, for example, from the data of one or of a plurality of the sensors 31, 32, 33.

In the control unit 35 the data of the sensors 31, 32, 33 are processed and compared to reference data stored in the control unit 35, whereupon the control unit 35 determines the state of the bank notes, in particular whether the bank notes are authentic.

Based on the check of the respective bank note carried out by the control unit 35, diverters 24, 26 arranged in the transport system 23 are activated, e.g. so as to store authentic bank notes in a first output pocket 25, while forged and/or bank notes suspected to be a forgery can be stored in a second output pocket 27. Via the transport system 23 the bank notes can also be supplied to a further processing 28, e.g. the destruction by means of a shredder or the storage in other output pockets.

Figure 2:
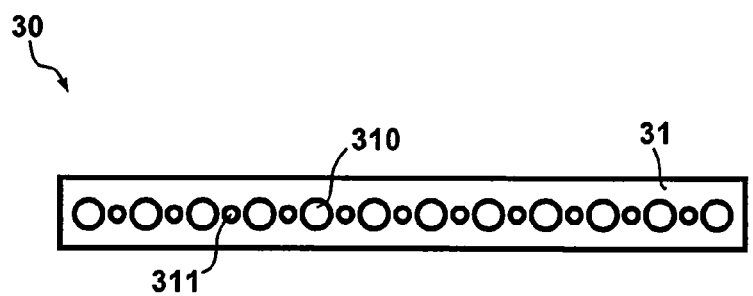
FIG. 2 shows an embodiment of a lighting means for a checking device.

FIG. 2 shows an embodiment of a lighting means 311 for a checking device, which for example is component of the first sensor 31. As previously described, the first sensor 31 detects light remitted by bank notes to be checked, which comes from the light source contained in the first sensor 31. The light source, too, can be a component of the first sensor 31 and for example be formed by several laser diodes 310 arranged in a line. As previously described, the laser diodes 310 forming the light source illuminate in a strip-shaped manner the bank notes to be checked. Additionally, there can also be present further optical elements such as mirrors, lenses, etc. so as to focus the light of the laser diodes 310 in a desired manner.

The device 10 for the check of bank notes is located in a housing 15, which for example only releases the input pocket 20 and the output pockets 25, 27. Light which comes from the light source or from the light sources of the sensor device 30 or the sensors 31, 32, 33, cannot emerge from the housing 15 during the operation of the device 10. It is ensured thereby that the above-described danger to the eyes of operators or service personnel is prevented. If the operator or the service personnel opens a door or flap 16 of the housing 15 so as to work in the area of the sensors 31, 32, 33, e.g. in order to remove bank notes jammed there, the light sources of the sensors 31, 32, 33 are switched off by the control unit 35 as soon as a device for the monitoring 17 connected with the door or flap 16, e.g. an interrupt switch, signals that the door or flap 16 is opened. Thus, also for the case of the opening of the housing 15 there can be ensured that a danger to the eyes of operators or service personnel cannot occur.

Alternatively or additionally, the sensor device 30 may also have a housing which during the operation prevents the emergence of light having a high radiant power. In this case, the housing of the sensor device 30 can be monitored, as previously described for the housing 15 of the device, in order to switch off the light sources of the sensors 31, 32, 33 as soon as light of the light sources can emerge from the housing. Likewise, the individual sensors 31, 32, 33 can be monitored and their light sources can be switched off if the emergence of the light of the light sources is possible.

After the light sources of the sensors 31, 32, 33 were switched off by the control unit 35, the operator or the service personnel can work within the device 10 and in particular work on the sensors 31, 32, 33 without any danger. During this work, however, it may be of disadvantage to the operator or the service personnel, when the light sources of the sensors 31, 32, 33 are switched off. For example, the removal of soil which has deposited on the sensors 31, 32, 33 may be more difficult, because the operator or the service personnel does not readily recognize the soil.

The lighting means 311 depicted in FIG. 2 consists of, for example, light emitting diodes, which similar to the laser diodes 310 are arranged in a line, e.g. always one light emitting diode 311 between two laser diodes 310. The lighting means 311 is switched on by the control unit 35 at the same time or after the laser diodes 310 forming the light sources of the sensors 31, 32, 33 have been switched off. The sensors 31, 32, 33 then are illuminated by the lighting means 311, although the light sources which are actually used for the operation are switched off. Service work on the sensors 31, 32, 33, e.g. the cleaning of a sensor window, can be carried out particularly well in this case, since the operator or the service personnel easily recognizes the soiling e.g. of a sensor window because of the lighting of the sensor window by the lighting means 311.

The lighting means 311 is advantageously configured such that it produces light of the same wavelength or of a wavelength range similar to that produced by the respective light source of the sensor 31, 32, 33. If the light sources of the respective sensor 31, 32, 33 produce light in the non-visible range, e.g. UV or IR light, the lighting means 311 can be chosen such that it produces light in the visible range.

In the embodiment depicted in FIG. 2 the lighting means 311 has a line structure which corresponds to the structure of the laser diodes 310 forming the light source of the first sensor 31. It is obvious that for the lighting means 311 there can be chosen a different structure. For example, there may be used more or less light sources for the lighting means 311 than the respective sensor has light sources 310, or the light sources of the lighting means 311 may have a spatial arrangement deviating from that of the light sources 310 of the respective sensor. Likewise, instead of light emitting diodes 311 other light sources may be used for the lighting means.

Deviating from the embodiment described hereinabove, wherein the lighting means 311 is formed by additional light sources, the light sources of the sensors 31, 32, 33 themselves can also be used for the lighting during a break in the normal operation upon which light may emerge from the housing 15 or the sensors 31, 32, 33. Here it may be provided, for example, that the light sources of the sensors 31, 32, 33 are operated with a lower electric current or a lower voltage, so that the radiant power of the light sources remains below a power endangering the eyes of the operator or service personnel. With this solution, however, there may occur the problem that in the case of an incorrect activation of the light sources of the sensors 31, 32, 33 the maximum permissible radiant power is exceeded. For this reason, the previously described solution is preferred, in which an additional lighting means independent of the light sources of the sensors 31, 32, 33 is provided, whose light sources 311 due to their construction cannot exceed the maximum permissible radiant power.

For safety reasons, it can also be provided that the at least one light source with high radiant power is switched off directly by the device for the monitoring 17, as soon as it has detected that light of the light source might pose a danger to the eyes of the operator or service personnel. The lighting means 311 here may also be switched on directly by the device for the monitoring 17.

If after the completion of the service work the housing 16 of the device 10 for the checking or the housing of the sensor device 30 is closed, normal operation can be resumed. In so doing, the lighting means 311 is switched off and the at least one light source with high radiant power is switched on again.

The invention claimed is:

1. A lighting arrangement for a checking device having at least one sensor which has at least one light source having high radiant power which represents a danger to the eyes of operators or service personnel, comprising a housing in which said at least one light source is contained and which when closed prevents emergence of light from the at least one light source outside the housing;
a monitor and switch arranged to detect the opening of the housing containing the at least one light source and switching off the at least one light source if the housing is opened;
another light source in the housing which has a radiant power not representing any danger to the eyes of operators or service personnel and that is arranged to be switched on at the same time or after an opening of the housing; and
a switch responsive to opening of the housing arranged to control at least said another light source.

2. The lighting arrangement for a checking device according to claim 1, wherein the switch comprises an electrical interrupt switch.

3. The lighting arrangement for a checking device according to claim 1, wherein the at least one light source comprises light emitting diodes.

4. The lighting arrangement for a checking device according to claim 1, wherein the properties of the another light source correspond to the properties of the at least one light source.

5. The lighting arrangement for a checking device according to claim 4, wherein the another light source has a wavelength or a wavelength range which corresponds to the wavelength or the wavelength range of the at least one light source.

6. The lighting arrangement for a checking device according to claim 4, wherein the light of the another light source has a spatial distribution which corresponds to the spatial distribution of the light of the at least one light source.

7. The lighting arrangement for a checking device according to claim 1, wherein the lighting arrangement is a component of the at least one sensor.

8. The lighting arrangement for a checking device according to claim 1, wherein the lighting arrangement produces visible light.

9. A method for the control of a lighting arrangement for a checking device having at least one sensor device comprising at least one light source, and wherein the at least one light source is contained in a normally closed housing that prevents emergence of light from the light source and radiates light with high radiant power which represents a danger to the eyes of operators or service personnel, comprising the steps:
monitoring the housing as to whether the housing is opened;
switching off the at least one light source if there is detected an opening of the housing, and
switching on at the same time as the opening or later another light source in the housing which has a radiant power not representing any danger to the eyes of operators or service personnel.

10. The method according to claim 9, wherein the another light source has properties which correspond to the properties of the at least one light source.

11. The method according to claim 10, wherein the another light source has a wavelength or a wavelength range which corresponds to the wavelength or the wavelength range of the at least one light source.

12. The method according to claim 10, wherein the light of the another source has a spatial distribution which corresponds to the spatial distribution of the light of the at least one light source.

13. The method according to claim 9, wherein the lighting arrangement produces visible light.

\* \* \* \* \*